US00PP35958P2

(12) United States Plant Patent
van der Meer

(10) Patent No.: US PP35,958 P2
(45) Date of Patent: Jul. 2, 2024

(54) ***ASTILBE* PLANT NAMED 'PRETTY IN PINK'**

(50) Latin Name: *Astilbe simplicifolia*
Varietal Denomination: Pretty in Pink

(71) Applicant: Hans van der Meer, Nieuwe Wetering (NL)

(72) Inventor: Hans van der Meer, Nieuwe Wetering (NL)

( * ) Notice: Subject to any disclaimer, the term of this patent is extended or adjusted under 35 U.S.C. 154(b) by 0 days.

(21) Appl. No.: 18/133,516

(22) Filed: Apr. 11, 2023

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
CPC ..... A01H 5/02; A01H 5/00; A01H 6/80
See application file for complete search history.

(56) References Cited

PUBLICATIONS

CPVO Register 4.10.10 for Astilbe Pretty in Pink, retrieved on Aug. 16, 2023 at https://online.plantvarieties.eu/publicConsultationDetails?registerId=20230843&denomination=pretty%20in%20pink, 3 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Astilbe* plant named 'Pretty in Pink', characterized by its broadly upright plant habit with outwardly arching inflorescences; vigorous growth habit; dark green-colored leaves; freely and uniformly flowering habit; long flowering period; pink-colored flowers on dark red-colored strong peduncles; and good container and garden performance.

2 Drawing Sheets

Figure 1:
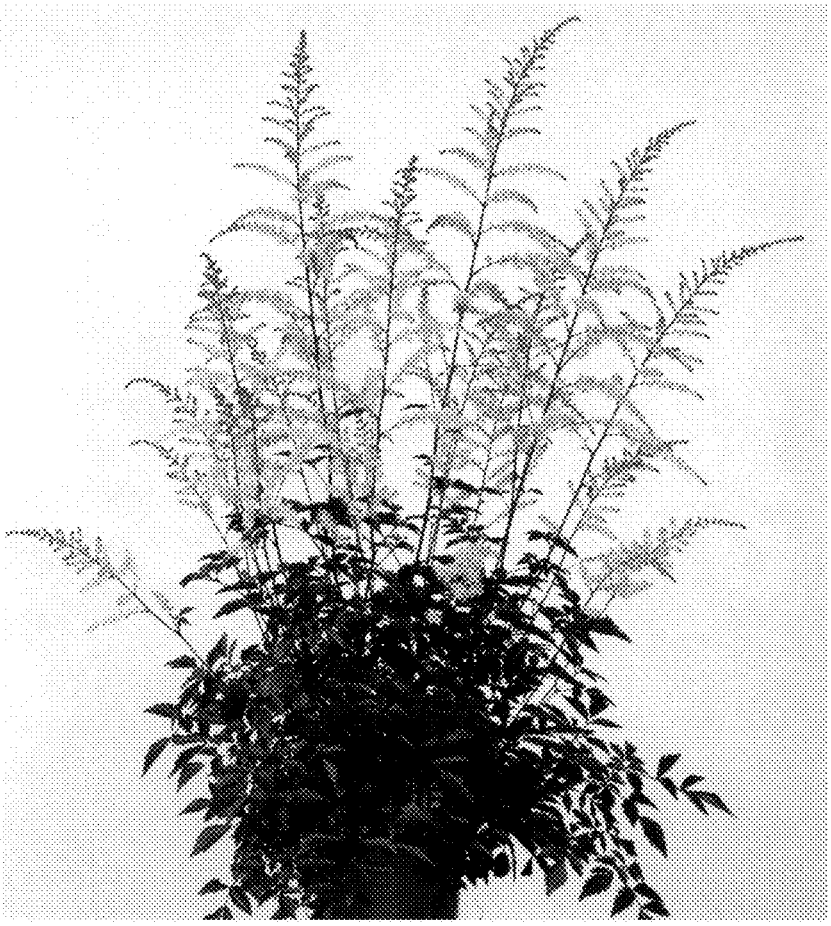

Botanical designation: *Astilbe simplicifolia.*
Cultivar denomination: 'PRETTY IN PINK'.

BACKGROUND OF THE INVENTION

The present invention relates to a new and distinct cultivar of *Astilbe*, botanically known as *Astilbe simplicifolia* and hereinafter referred to by the name 'Pretty in Pink'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from an open-pollination in 2015 in Nieuwe Wetering, The Netherlands, of an unidentified seedling selection of *Astilbe simplicifolia*, not patented, as the female, or seed, parent with an unknown seedling selection of *Astilbe simplicifolia* as the male, or pollen, parent. The new *Astilbe* plant was discovered and selected by the Inventor as a single flowering plant from within the progeny of the stated open-pollination in a controlled greenhouse environment in Nieuwe Wetering, The Netherlands during the summer of 2017.

Asexual reproduction of the new *Astilbe* plant by vegetative divisions in a controlled nursery environment in Nieuwe Wetering, The Netherlands since December, 2017, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pretty in Pink'. These characteristics in combination distinguish 'Pretty in Pink' as a new and distinct *Astilbe* plant:

1. Broadly upright plant habit with outwardly arching inflorescences.
2. Vigorous growth habit.
3. Dark green-colored leaves.
4. Freely and uniformly flowering habit.
5. Long flowering period.
6. Pink-colored flowers on dark red-colored strong peduncles.
7. Good container and garden performance.

Plants of the new *Astilbe* differ primarily from plants of the female parent selection in the following characteristics:

1. Plants of the new *Astilbe* are taller and more vigorous than plants of the female parent selection.
2. Plants of the new *Astilbe* flower for a longer period of time than plants of the female parent selection.
3. Plants of the new *Astilbe* have taller (longer) and more arching inflorescences than plants of the female parent selection.
4. Stems and peduncles of pants of the new *Astilbe* are dark red in color whereas stems and peduncles of plants of the female parent selection are green in color.

Plants of the new *Astilbe* can be compared to plants of *Astilbe simplicifolia* 'Hennie Graafland', not patented. In side-by-side comparisons, plants of the new *Astilbe* and 'Hennie Graafland' differ primarily in the following characteristics:

1. Plants of the new *Astilbe* are taller and more vigorous than plants of 'Hennie Graafland'.
2. Plants of the new *Astilbe* have larger leaves than plants of 'Hennie Graafland'.
3. Plants of the new *Astilbe* have larger flowers than plants of 'Hennie Graafland'.
4. Plants of the new *Astilbe* flower for a longer period of time than plants of 'Hennie Graafland'.
5. Plants of the new *Astilbe* have taller (longer) and more arching inflorescences than plants of 'Hennie Graafland'.
6. Stems and peduncles of plants of the new *Astilbe* are dark red in color whereas stems and peduncles of plants of 'Hennie Graafland' are green in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1) is a side perspective view of a typical flowering plant of 'Pretty in Pink' grown in a container.

Figure 2:
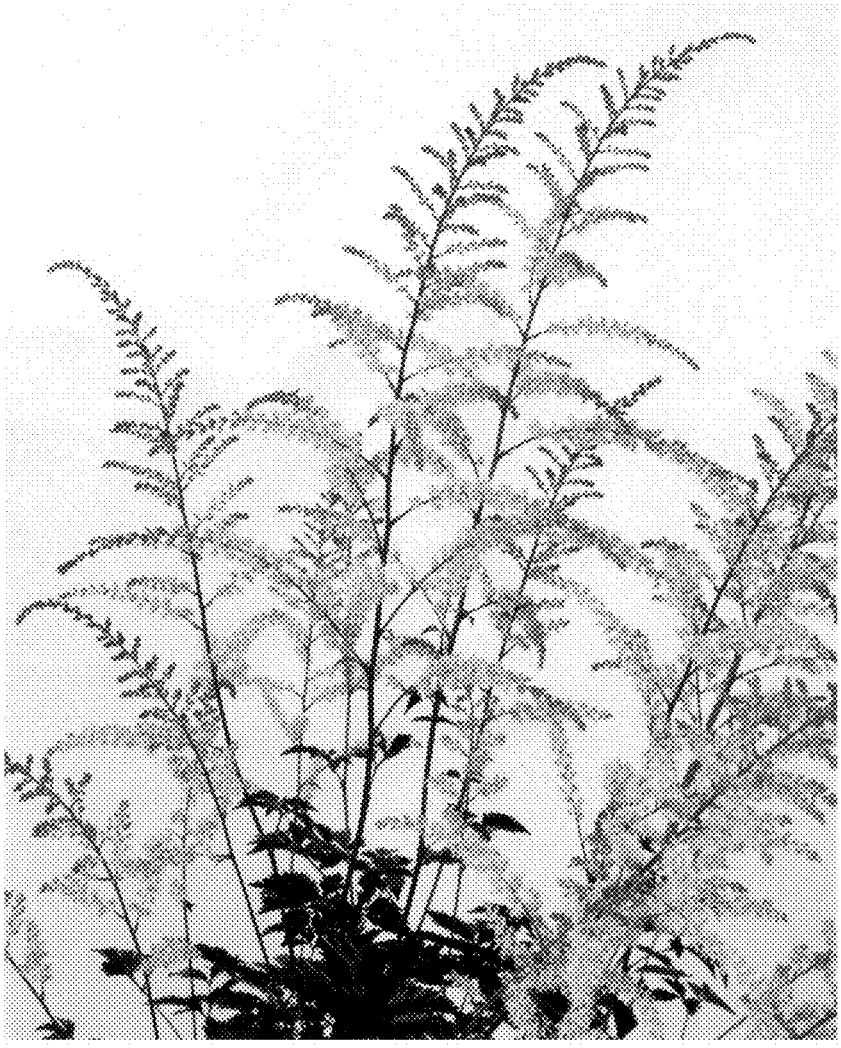

The photograph on the second sheet (FIG. 2) is a close-up view of typical inflorescences of 'Pretty in Pink'.

DETAILED BOTANICAL DESCRIPTION

The aforementioned photographs and following observations, measurements and values describe plants grown during the late summer in 15-cm containers in an outdoor nursery in Nieuwe Wetering, The Netherlands and under cultural practices typical of commercial *Astilbe* production. During the production of the plants, day temperatures ranged from 18C to 34C and night temperatures ranged from 10C to 20C. Plants were one year old when the photographs and description were taken. In the following description, color references are made to The Royal Horticultural Society Colour Chart, 2015 Edition, except where general terms of ordinary dictionary significance are used.

Botanical classification: *Astilbe simplicifolia* 'Pretty in Pink'.

Parentage:

*Female, or seed, parent.*—Unidentified seedling selection of *Astilbe simplicifolia*, not patented.

*Male, or pollen, parent.*—Unknown seedling selection of *Astilbe simplicifolia*, not patented.

Propagation:

*Type.*—By vegetative divisions.

*Time to initiate roots.*—About three weeks at temperatures about 20C.

*Root description.*—Thick, fleshy; typically brown in color, actual color of the roots is dependent on substrate composition, water quality, fertilizer type and formulation.

*Rooting habit.*—Freely branching; dense.

Plant description:

*Plant form and growth habit.*—Herbaceous perennial; broadly upright plant habit with outwardly arching inflorescences with inflorescences held above the foliar plane on strong peduncles; flowering stems and leaves basal; freely flowering with numerous basal branches developing per plant, dense and bushy appearance; vigorous growth habit; and freely and uniformly flowering habit.

*Growth rate.*—Moderately rapid; from divisions, about three months are required to produce fully-grown flowering plants in containers.

*Plant height* (*soil level to top of foliar plane*).—About 32.4 cm.

*Plant height* (*soil level to top of inflorescences*).—About 65.5 cm.

*Plant width* (*spread*).—About 69 cm.

*Stem description.*—Quantity per plant: About 22 basal branches per plant. Length: About 28.1 cm. Diameter: About 2.5 mm. Internode length: About 11.7 cm. Strength: Strong. Aspect: Erect to about 22.5 degrees from vertical. Texture and luster: Sparsely pubescent; pubescence minute; glossy. Color, developing: Close to 146C. Color, at the internodes: Close to 182A. Color, developed: Close to 146A; on sun-exposed surfaces, strongly tinged with close to a blend of 183A and 200D.

Leaf description:

*Arrangement.*—Alternate; biternately compound; on average, about 27 leaflets per leaf.

*Leaf length* (*excluding petiole*).—About 15.7 cm.

*Leaf width.*—About 15.7 cm.

*Terminal leaflet length.*—About 4.7 cm.

*Terminal leaflet width.*—About 2.1 cm.

*Lateral leaflet length.*—About 2.8 cm.

*Lateral leaflet width.*—About 1.4 cm.

*Leaf shape, in outline.*—Broadly ovate to broadly rhomboidal.

*Leaflet shape.*—Elliptic to narrowly elliptic to narrowly ovate.

*Leaflet apex.*—Narrowly acute.

*Leaflet base.*—Attenuate to narrowly cuneate; occasionally, obtuse.

*Leaflet margin.*—Biserrate.

*Leaflet texture and luster, upper surface.*—Moderately pubescent on the midvein and lateral venation; glossy.

*Leaflet texture and luster, lower surface.*—Moderately pubescent on the midvein and lateral venation; moderately glossy.

*Leaflet venation pattern.*—Pinnate.

*Leaflet color.*—Developing leaflets, upper surface: Close to 137A. Developing leaflets, lower surface: Close to a blend of 146A and 147B. Fully expanded leaflets, upper surface: Slightly darker than a blend of NN137B and 147A; venation, close to 144A. Fully expanded leaflets, lower surface: Close to 146A; venation, close to 146C and 146D.

*Leaf petiole length.*—About 19 cm.

*Leaf petiole diameter.*—About 2 mm.

*Leaf and leaflet petiole strength.*—Strong.

*Leaf and leaflet petiole texture and luster, upper and lower surfaces.*—Sparsely pubescent; moderately glossy.

*Leaf and leaflet petiole color, upper surface.*—Close to 146A tinged with close to 148A.

*Leaf and leaflet petiole color, lower surface.*—Close to 146C.

Flower description:

*Flower type and flowering habit.*—Single rotate flowers arranged on outwardly arching terminal compound panicles; flowers face upright, outward or downward depending on position on the inflorescence; panicles conical in shape; freely and uniformly flowering habit with about 2,100 flowers developing per inflorescence and about 45,000 flowers developing per plant during the flowering season.

*Fragrance.*—Strong; sweet and pleasant.

*Natural flowering season.*—Plants begin flowering about 100 days after planting; continuously flowering from late spring until late summer in The Netherlands.

*Postproduction longevity.*—Flowers last about ten days on the plant; flowers not persistent.

*Flower buds.*—Height: About 2 mm. Diameter: About 1.5 mm. Shape: Broadly elliptic. Texture and luster: Smooth, glabrous; matte. Color: Sepals, close to 144C and petals, close to 63A.

*Inflorescence height.*—About 30.3 cm.

*Inflorescence diameter.*—About 19.4 cm.

*Flower diameter.*—About 6 mm by 6 mm.

*Flower depth.*—About 3.5 mm.

*Petals.*—Quantity per flower: Typically five in a single whorl. Length: About 3.5 mm. Width: About 0.8 mm. Shape: Oblanceolate. Apex: Obtuse. Base: Narrowly cuneate. Margin: Entire; not undulate. Texture and luster, upper and lower surfaces: Smooth, glabrous; matte. Color: Developing petals, upper and lower surfaces: Close to 69D. Fully expanded petals, upper and lower surfaces: Close to NN155D; color does not change with subsequent development.

*Sepals.*—Quantity per flower: Typically five in a single whorl; towards the base forming a campanulate-shaped calyx. Calyx length: About 2 mm. Calyx diameter: About 2.5 mm. Length: About 2 mm. Width: About 0.8 mm. Shape: Ovate. Apex: Bluntly acute. Base: Cuneate, fused. Margin: Entire. Texture and luster, upper and lower surfaces: Smooth, glabrous; matte. Color: Developing sepals, upper surface: Close to NN155B; towards the apex and margins, close to 64C. Developing sepals, lower surface: Close to NN155B; towards the apex, close to 64C. Fully expanded sepals, upper and lower surfaces: Close to 150D; towards the apex, close to 63D; color does not change with subsequent development.

*Peduncles.*—Length: About 30 cm. Diameter: About 2 mm. Angle: Mostly erect. Strength: Strong. Texture and luster: Densely pubescent; moderately glossy. Color: Close to 178A.

*Pedicels.*—Length: About 1.5 mm. Diameter: About 0.5 mm. Angle: About 40 degrees from peduncle axis. Strength: Moderately strong. Texture and luster: Moderately pubescent; matte. Color: Close to 145A.

*Reproductive organs.*—Stamens: Quantity per flower: Typically ten. Filament length: About 2 mm. Filament color: Close to 70C. Anther shape: Broadly ovate. Anther length: About 0.5 mm. Anther diameter: About 0.25 mm. Anther color: Close to N155B. Pollen amount: Scarce. Pollen color: Close to NN155A. Pistils: Quantity per flower: Two. Pistil length: About 2 mm. Stigma diameter: About 0.25 mm. Stigma shape: Club-shaped. Stigma color: Close to 70C. Style length: About 1 mm. Style color: Close to 62C. Ovary color: Close to 65D.

*Seeds and fruits.*—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25C to 35C and to be suitable for USDA Hardiness Zones 5 through 10.

It is claimed:

1. A new and distinct *Astilbe* plant named 'Pretty in Pink' as illustrated and described.

* * * * *